United States Patent [19]

DeBaun et al.

[11] 4,234,593
[45] Nov. 18, 1980

[54] 3-(N-ALKYLCARBAMYL)-5-(CARBOALKOXY)-1,3,4-OXADIAZOLE-2-THIONES AND THEIR USE AS ANTI-INFLAMMATORY AGENTS

[75] Inventors: Jack R. DeBaun, Sunnyvale; Ferenc M. Pallos, Walnut Creek; Arnold D. Gutman, Berkeley, all of Calif.

[73] Assignee: Stauffer Chemical Company, Westport, Conn.

[21] Appl. No.: 22,129

[22] Filed: Mar. 20, 1979

[51] Int. Cl.$^2$ .................. A61K 31/42; C07D 271/10
[52] U.S. Cl. ........................... 424/272; 548/144
[58] Field of Search ............... 260/307 C; 548/143, 548/144; 424/272

Primary Examiner—Jose Tovar
Attorney, Agent, or Firm—Edwin H. Baker

[57] ABSTRACT

3-(N-Alkylcarbamyl)-5-(carboalkoxy)-1,3,4-oxadiazole-2-thione compound having the structural formula

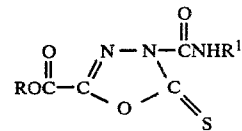

wherein R is alkyl having 1 to 4 carbon atoms and R$^1$ is alkyl having 1 to 4 carbon atoms, and their use as anti-inflammatory agents.

3 Claims, No Drawings

3-(N-ALKYLCARBAMYL)-5-(CARBOALKOXY)-1,3,4-OXADIAZOLE-2-THIONES AND THEIR USE AS ANTI-INFLAMMATORY AGENTS

BACKGROUND OF THE INVENTION

This invention relates to 3-(N-alkylcarbamyl)-5-(carboalkoxy)-1,3,4-oxadiazole-2-thiones which are useful as anti-inflammatory agents.

BRIEF DESCRIPTION OF THE INVENTION

The compound of this invention has the following structural formula:

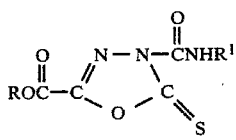

wherein R is alkyl having 1 to 4 carbon atoms, preferably 1 to 2 carbon atoms and $R^1$ is alkyl having 1 to 4 carbon atoms, preferably 1 to 2 carbon atoms.

The compounds can be prepared according to the teaching of the following example.

EXAMPLE I 3-(N-methylcarbamyl)-5-(carboethoxy)1,3,4-oxadiazole-2-thione

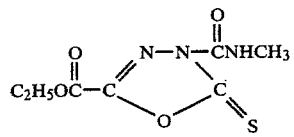

3.4 grams (g) of the 5-(carboethoxy)1,3,4-oxadiazole-B 2-thione reactant and 3 milliliters (ml) CH$_3$NCO were combined in a 125 ml Erlenmeyer flask with 50 ml of acetone. After the exothermic reaction had ceased, the reaction mixture was poured into 200 ml benzene, washed with water, dried and separated. 2.5 g of the desired product was obtained, melting point (m.p.) 67°–71° C. The product of the example will hereinafter be called compound No. 1.

ANTI-INFLAMMATORY SCREENING

The compounds of the present invention have pharmaceutical activity especially as anti-inflammatory agents. Anti-inflammatory activity is demonstrated by a test which involves the diminution of experimental edema induced in the hind paw of the rat by the injection of carrageenin.

Carageenin injected into the foot of the rat produces an edematous condition which simulates part of the inflammatory process. Non-steroidal anti-inflammatory compounds inhibit the formation of this edema.

ANTI-EDEMA

Anti-edema effect was determined according to the test procedure recited by Winter, C. A., Risley, E. A., and Nuss, G. W., Proc. Exper. Biol. Med. 111:544–547, 1962. For this test, three male Wistar rats (Taiwan strain) weighing 100–120 g each are orally dosed with test compound dissolved or suspended in 3 ml of water. One hour later, the plantar surface of the right hind paw was injected with 0.1 ml of a 1 percent suspension of carrigeenan in saline and the left paw was similarly injected with saline only. Three hours after the injection the volume of both hind paw was measured by fluid displacement and the percent decrease in carrigeenan-induced swelling (volume of carrigeenan injected foot minus saline injected foot) was determined by comparison with untreated (no test compound) animals. Greater than 30 percent inhibition is considered evidence of an anti-edema effect.

Table 1 shows the reduction in edema in the hind paw of a rat according to the above-described test procedure at the rate indicated.

TABLE 1

| Compound Number | Percent Reduction in Edema | |
|---|---|---|
| | Rate mg/kg | Reduction of Induced Edema |
| 1 | 100 | 59% |
| phenylbutazone (standard) | 100 | 41% |

The compound of the present invention, either alone of in the form of pharmaceutical composition may be administered to an animal subject in any of a number of forms and via any of several routes. Thus, the compound or composition thereof may be orally administered in the form of tablets, pills, capsules, or in the form of a suspension. The compound may also be administered parenterally in the form of an injectable solution or suspension. The compound or composition thereof may also be administered topically, in the form of an ointment or rectally, in the form of a suppository.

When orally administering the compound or composition, use can be made of a tablet, pill or capsule consisting entirely of the desired compound, although ordinarily, a composition comprising an effective amount of the compound and varying amounts of one or more physiologically inert materials such as carriers, vehicles, binders and the like will be used. Additionally, the compound may be orally administered in the form of a suspension thereof in a suitable vehicle such as a syrup.

When parenterally administering the compound or composition, use may be made of a parenteral solution or suspension of the compound in a suitable solvent or suspension medium.

The compound of the present invention may also be administered rectally in the form of a suppository comprising an effective amount of the desired compound and a suitable vehicle such as petroleum jelly.

What we claim:

1. A compound having the following structural formula:

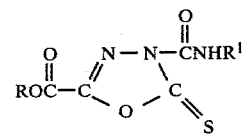

wherein R is alkyl having 1 to 4 carbon atoms and $R^1$ is alkyl having 1 to 4 carbon atoms.

2. The compound of claim 1 wherein R is ethyl and $R^1$ is methyl.

3. A method of treatment of an inflammatory condition in a mammal comprising administering to said mammal a therapeutically effective amount of a compound having the following structural formula:

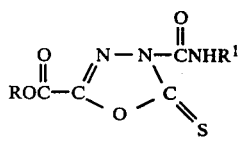
wherein R is alkyl having 1 to 4 carbon atoms and $R^1$ is alkyl having 1 to 4 carbon atoms.
* * * * *
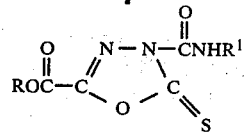
wherein R is alkyl having 1 to 4 carbon atoms and $R^1$ is alkyl having 1 to 4 carbon atoms.
* * * * *